US009550510B2

United States Patent
Huguet et al.

(10) Patent No.: US 9,550,510 B2
(45) Date of Patent: Jan. 24, 2017

(54) ADJUSTABLE HANDLE SYSTEM FOR A PUSH CART

(71) Applicant: Howard Industries, Ellisville, MS (US)

(72) Inventors: Jared Huguet, Petal, MS (US); David Schoenfeld, Petal, MS (US); Tony Thornton, Hattiesburg, MS (US)

(73) Assignee: HOWARD INDUSTRIES, Ellisville, MS (US)

( * ) Notice: Subject to any disclaimer, the term of this patent is extended or adjusted under 35 U.S.C. 154(b) by 0 days.

(21) Appl. No.: 15/048,436

(22) Filed: Feb. 19, 2016

(65) Prior Publication Data
US 2016/0272232 A1 Sep. 22, 2016

Related U.S. Application Data

(60) Provisional application No. 62/119,258, filed on Feb. 22, 2015.

(51) Int. Cl.
*B62B 3/06* (2006.01)
*B62B 5/06* (2006.01)
*B62B 3/02* (2006.01)

(52) U.S. Cl.
CPC ........ *B62B 5/065* (2013.01); *B62B 3/02* (2013.01)

(58) Field of Classification Search
CPC ............ B62B 5/06; B62B 5/064; B62B 5/065; B62B 5/066; B62B 3/02; B62B 3/022; B62B 3/025
USPC ................... 280/47.34, 47.36, 47.371, 655.1
See application file for complete search history.

(56) References Cited

U.S. PATENT DOCUMENTS

| 7,017,936 B2 * | 3/2006 | Huang | B62B 9/20 280/47.371 |
| 7,766,367 B2 * | 8/2010 | Dotsey | B62B 7/086 280/647 |
| 8,196,939 B2 * | 6/2012 | Bustle | A47B 21/0314 280/47.35 |

OTHER PUBLICATIONS

Tim Barden et al., "Steering Assist System for a Push Cart", U.S. Appl. No. 62/119,252, filed Feb. 22, 2015.

* cited by examiner

*Primary Examiner* — John Walters
(74) *Attorney, Agent, or Firm* — Finnegan, Henderson, Farabow, Garrett & Dunner, LLP

(57) ABSTRACT

The present disclosure describes a cart having an adjustable handle system, the cart having: a chassis supported on wheels; a horizontal work surface having a perimeter defined by at least a front edge, a rear edge, and two side edges; a stationary handle connected to, and extending along the perimeter of the horizontal work surface from an origination point located on the rear edge to a connecting point located on one of the two side edges; a moveable handle axially coupled to the stationary handle at the connecting point and extending along the perimeter of the horizontal work surface from the connecting point to an end point located on the front edge; and an adjustable connecting device connecting the moveable handle to the stationary handle at the connecting point and controlling the angular position of the moveable handle relative to the stationary handle.

7 Claims, 8 Drawing Sheets

ADJUSTABLE HANDLE SYSTEM FOR A PUSH CART

CROSS-REFERENCE TO APPLICATION

This application claims the benefit of and incorporates by reference, in its entirety, the contents of U.S. Provisional Application No. 62/119,258, filed Feb. 22, 2015, and entitled "Adjustable Handle System For A Push Cart." This application further incorporates by reference, in its entirety, the contents of U.S. Provisional Application No. 62/119,252, filed Feb. 22, 2015 (now U.S. application Ser. No. 15/048,425, filed Feb. 19, 2016), and entitled "Steering Assist System for a Push Cart."

FIELD OF THE DISCLOSURE

The present disclosure relates to an adjustable handle system for a push cart and, more particularly, to a point-of-care medical cart having an adjustable handle system for improved control and ergonomic comfort when the cart is being moved. Though the disclosure will primarily refer to a medical cart in a health-care environment, it should be appreciated that the adjustable handle system may be incorporated into other mobile machines and that the adjustable handles and/or push cart may be used in other non-health care environments.

BACKGROUND OF THE DISCLOSURE

Medical carts are among the most widespread tools used in the health care industry, and similar push carts are increasingly being used in other environments, such as factories, garages, workshops, and offices. Medical carts are designed for a variety of uses and environments, but some function, e.g., as mobile computing workstations that allow health-care professionals to access, input, and distribute patients' medical information and/or medical treatment. For example, a nurse or other medical practitioner may use a medical cart equipped with a computer and/or diagnostic equipment while making rounds between patients in a hospital or other care facility. The practitioner may use the computer, e.g., to review a patient's medication information, record vital signs and other notes, and order treatment. Medical carts may be equipped with tools for diagnosis and treatment, and/or store and dispense medication. Regardless of the cart's specific purpose, however, the cart must be configured to move quickly but safely through a hospital environment.

Providing a medical cart that can easily move through a hospital presents several challenges. For example, modern medical carts often include a computer, display screens, an adjustable keyboard, an independent power system, extra-capacity batteries, large height-adjustable work-surfaces, and storage for medication or equipment—weighing tens to hundreds of pounds. The mass of the cart may make it difficult to control in tight areas, such as hospital rooms. Injuries are more likely to occur if the cart is not ergonomically designed. Although various "battery-assisted" solutions for improving control and maneuverability exist, they do not fully address the problem.

Moreover, although many medical carts are ergonomically designed to lessen fatigue and reduce musculoskeletal disorders associated with the use of an on-board computer, e.g., by providing the ability to adjust the height of the monitor and/or keyboard so a user can type in an ergonomic position, little consideration is given to the health professional while he or she is moving the medical cart between locations. Therefore, there exists a need for designs that improve control, safety, and ergonomic comfort during movement of the cart.

SUMMARY OF THE DISCLOSURE

In the following description, certain aspects and embodiments of the present disclosure will become evident. It should be understood that the disclosure, in its broadest sense, could be practiced without having one or more features of these aspects and embodiments. It should also be understood that these aspects and embodiments are merely exemplary.

In one embodiment, the present disclosure provides a cart having an adjustable handle system, the cart comprising: a chassis supported on wheels; a horizontal work surface having a perimeter defined by at least a front edge, a rear edge, and two side edges; a stationary handle connected to, and extending along the perimeter of the horizontal work surface from an origination point located on the rear edge to a connecting point located on one of the two side edges; a moveable handle axially coupled to the stationary handle at the connecting point and extending along the perimeter of the horizontal work surface from the connecting point to an end point located on the front edge; and an adjustable connecting device connecting the moveable handle to the stationary handle at the connecting point and controlling the angular position of the moveable handle relative to the stationary handle.

In its normal position, the moveable handle may assume a generally horizontal position flush with the stationary handle that surrounds the outer perimeter of the console. Thus, the moveable handle remains continuous and in line with at least a part of the wrap-around handle, which is easy to grab from any direction.

When needed, the moveable handle can be rotated toward a vertical position. Accordingly, the moveable handle can be positioned at an angle very near the natural position of the hands, so as to provide for increased control and maneuverability of the cart in tight areas.

In another embodiment, the cart further comprises a computer and a display screen; and a handle feedback controller that monitors the angular movement and/or position of the moveable handle relative to the stationary handle, wherein the handle feedback controller activates a function of the computer.

Other aspects of the disclosure will become more apparent from the detailed description of the exemplary embodiments. It is to be understood that both the foregoing general description and the following detailed description are exemplary and explanatory only, and are not restrictive of the disclosed embodiments, as claimed.

DETAILED DESCRIPTION

Figure 1:
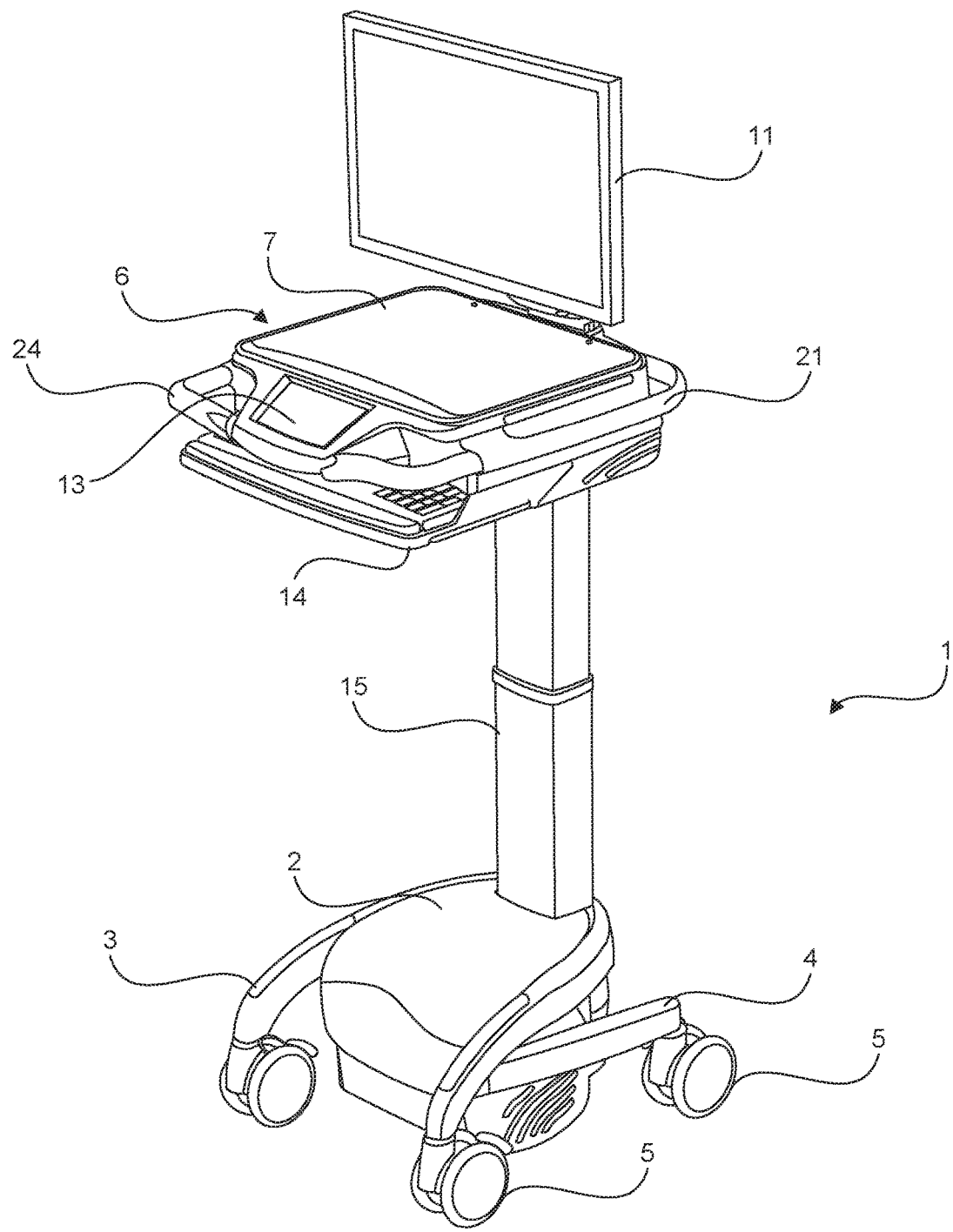
FIG. 1 is a front perspective view of an exemplary medical cart with an adjustable handle system for improved control and ergonomic comfort, according to an exemplary disclosed embodiment.

Reference will now be made in detail to the exemplary embodiments of the present disclosure described above and illustrated in the accompanying drawings. As shown in FIG. 1, an exemplary push cart 1, in this case a point-of-care medical cart 1 may include a chassis or base 2 supported on wheels. For example, the cart chassis or base 2 may be supported on caster-type wheels 5 that can swivel 360° around a vertical axis, thereby facilitating movement of the cart in all directions. The chassis 2 may also include, for example, upper legs 3 and lower legs 4. Each of the upper and lower legs 3, 4 may be connected to a respective caster wheel 5. The cart may also include a steering assist system (not shown) that interacts with the wheels 5 to help control movement of the cart 1, e.g., by preventing the wheels 5 from swiveling toward the inside.

Figure 2:
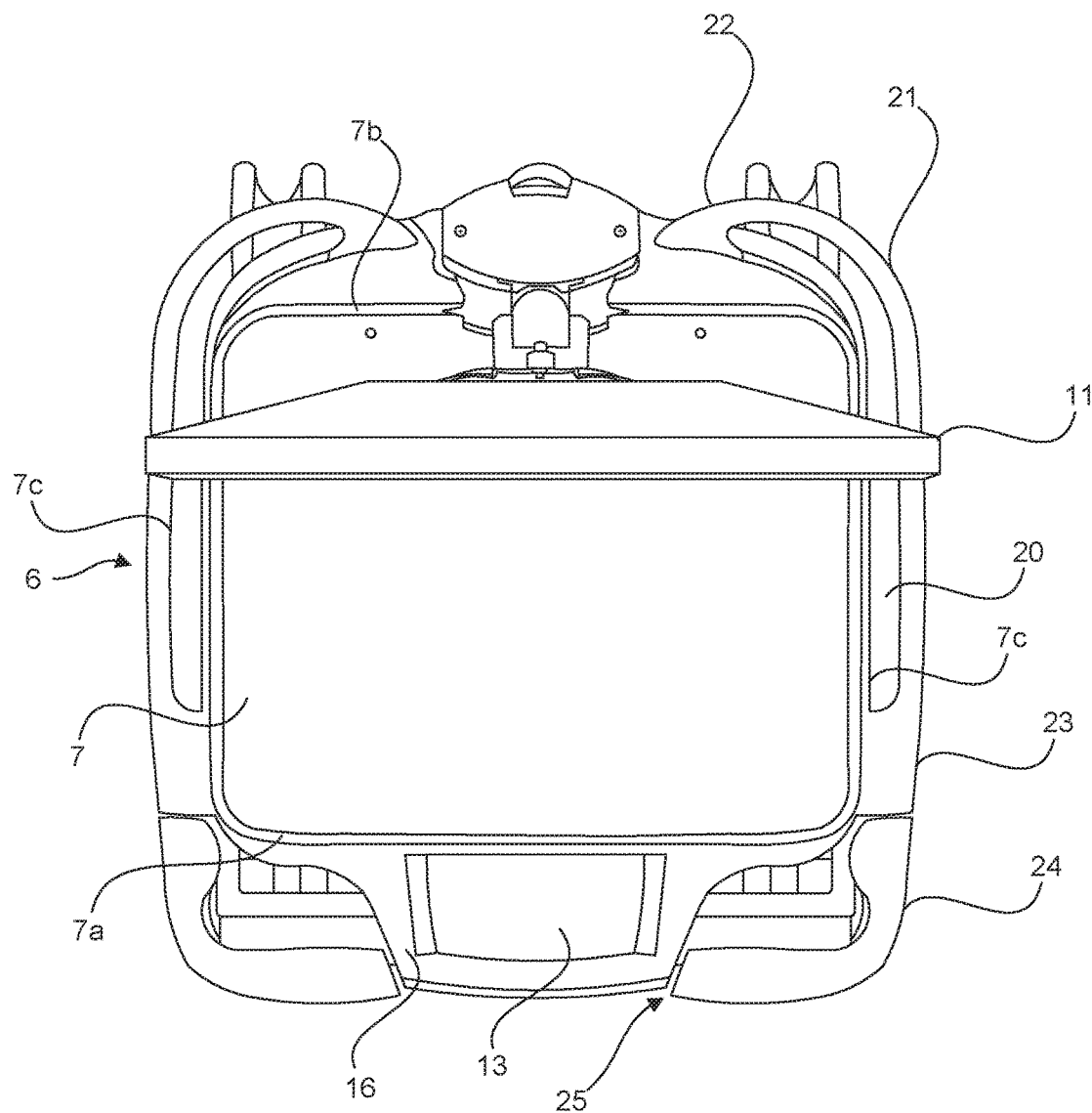
FIG. 2 is a top view of the medical cart of FIG. 1.

As shown in FIGS. 1 and 2, the cart 1 may also include a console 6 having a work surface 7, a computing device (not shown) mounted in the console 6 below the work surface 7, and an adjustable display screen 11 mounted above the work surface 7. The work surface 7 may be horizontal and have a perimeter defined by a front edge 7a, a rear edge 7b, and two side edges 7c. The console 6 and/or display screen 11 can be mounted to an adjustable column 15 that allows the height of the console 6 and/or display screen 11 to be adjusted. The cart 1 may also include a control panel 13 that allows a user to control the computing device and other components of the cart 1. For example, the control panel 13 shown in FIGS. 1 and 2 includes a touchscreen (e.g., an LCD screen) that is integrated into a projecting portion 16 of the console 6 in front of the work surface 7. The cart 1 may also Include an input device tray 14, such as a keyboard and/or mouse tray, located below the control panel 13. Although not shown, the chassis 2 may include a power supply, including, e.g., a rechargeable battery, for supplying power to the cart and its components.

Figure 3A:
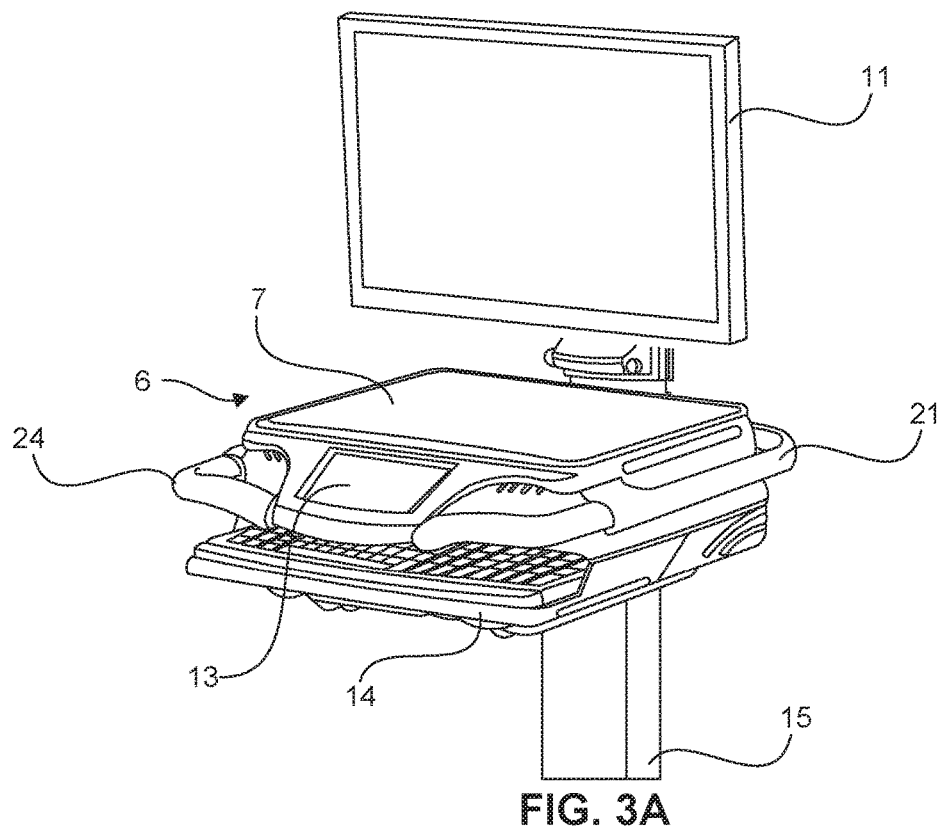
FIGS. 3A and 3B are front perspective views of the medical cart of FIG. 1, illustrating two exemplary positions for a moveable handle that is part of the adjustable handle system.
Figure 3B:
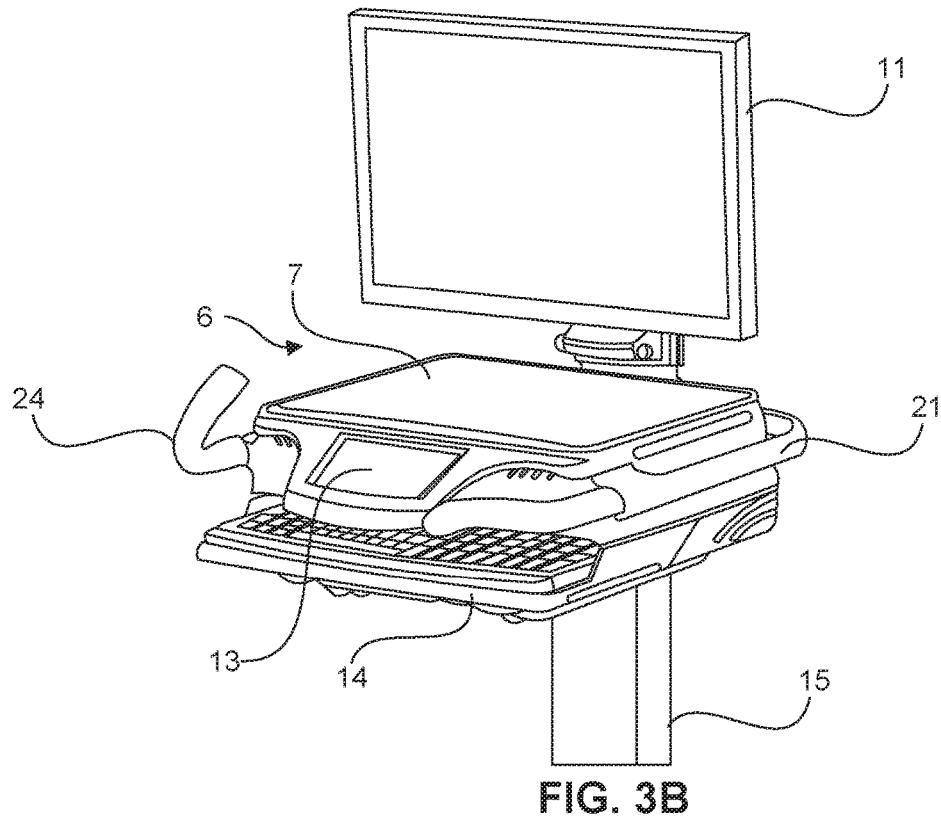
Figure 4:
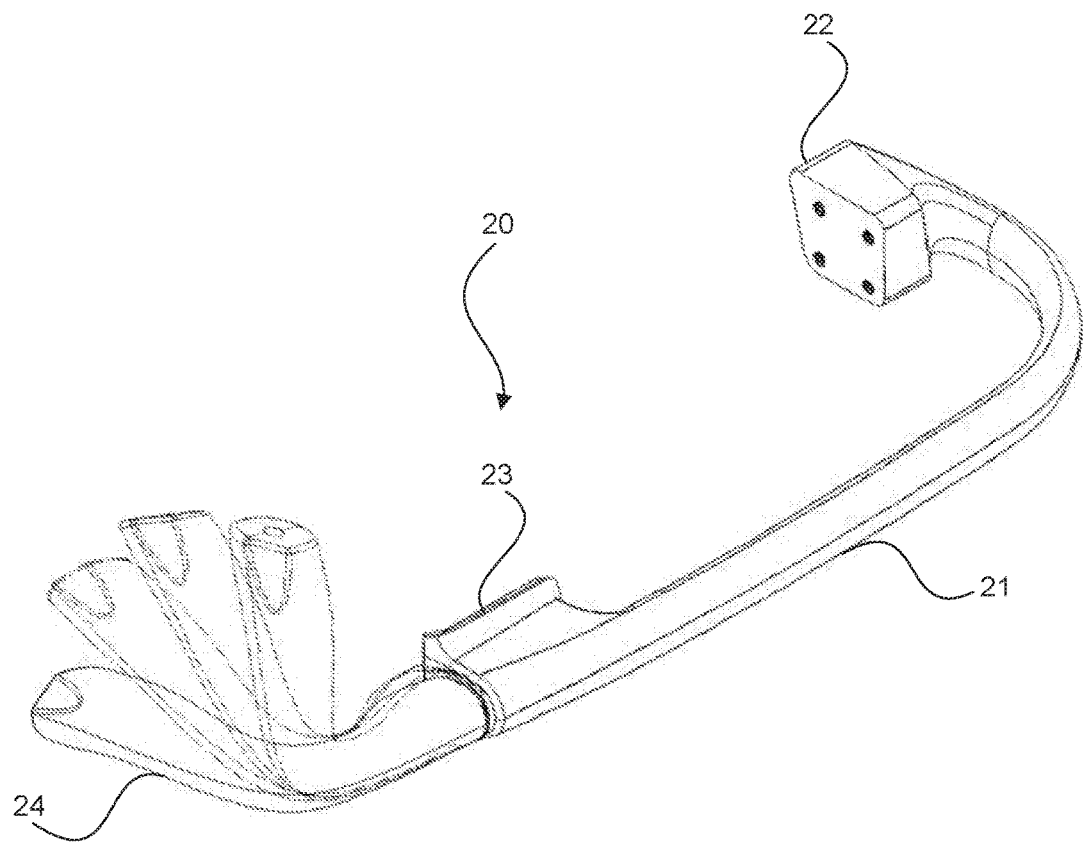
FIG. 4 is a perspective view of the adjustable handle system removed from the medical cart of FIG. 1, showing the operation of the moveable handle.

With reference to FIGS. 2-4, the cart 1 has an adjustable handle system 20 that extends around the perimeter of the console 6. The adjustable handle system 20 may include one or more stationary handles 21 extending along the perimeter of the work surface 7, e.g., from an origination point 22 located on the rear edge 7b of the console 6 to a connecting point 23 located on one of the two side edges 7c. In some embodiments, the stationary handle 21 may be connected to the perimeter of the console 6 only at the origination point 22 and the connecting point 23, such that the stationary handle 21 and the perimeter of the console 6 are separated by a gap 26 extending the length of the stationary handle 21 between the origination point 22 and the connecting point 23. In other embodiments, the stationary handle 21 may be connected to the console 6 at multiple intermediate positions, or continuously along the perimeter of the console 6, e.g., so as to form a bulbous rim around the perimeter of the console or work surface.

The gap 26 between the stationary handle 21 and the perimeter of the console 6 may be sized to allow a user's hand to move freely therethrough. The cross-section of the stationary handle 21 may be oval or another ergonomic shape, and may have a cross-section that varies along its length. The adjustable handle system 20 may also comprise a moveable handle 24 that is axially coupled to each stationary handle 21 at a respective connecting point 23.

As illustrated in the embodiment of FIG. 3A, the moveable handle 24 may extend along the perimeter of the console 6 from the connecting point 23 to an end point 25 located on the front edge 7a of the console, such that the moveable handle 24 is flush with a side of the projecting portion 16 in the center of the console. The moveable handle 24 may also include one or more buttons or other controls (not shown), e.g., a touchpad or other cursor control, on its end, or elsewhere along its length. As will be explained in more detail below, an adjustable connecting device 40 connecting the moveable handle 24 to the stationary handle 21 may be used to control the angular position of the moveable handle 24 relative to the stationary handle 21, such that the moveable handle 24 may be rotated, for example, from the position in FIG. 3A to the position in FIG. 3B.

Figure 5:
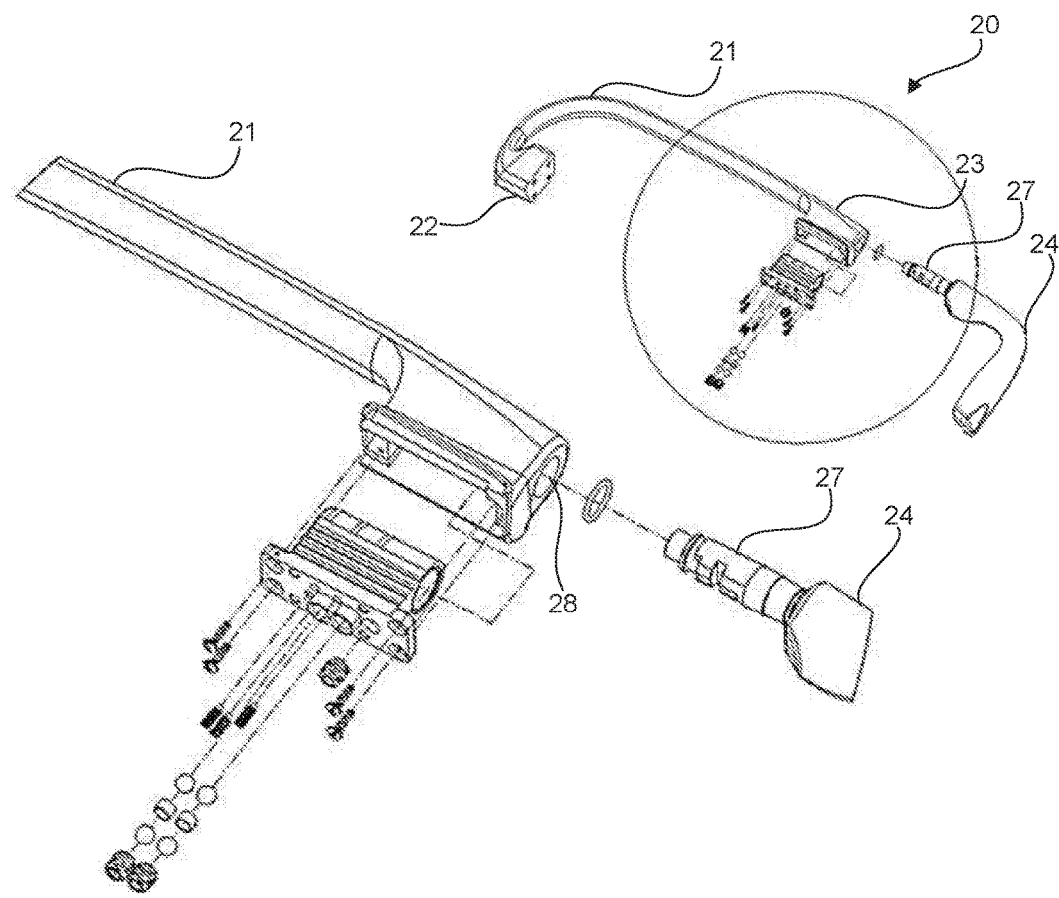
FIG. 5 is a partial exploded view of the adjustable handle system of FIG. 4, showing an adjustable connecting device connecting the moveable handle to the stationary handle according to an exemplary disclosed embodiment.

In FIGS. 4-5, the adjustable handle system 20 is shown removed from the cart 1 of FIG. 1. The moveable handle 24 is connected to the stationary handle 21 at the connecting point 23 by the adjustable connecting device 40 that allows a user to control the angular position of the moveable handle 24 relative to the stationary handle 21. The adjustable connecting device 40 may include a trunnion shaft 27 attached to and extending from the moveable handle 24 into a cavity 28 formed in the stationary handle 21. The trunnion shaft 27 is a cylindrical projection that is used as an axis of rotation for the moveable handle 24. In another embodiment, the trunnion shaft 24 is attached to, and extends from the stationary handle 21 into a cavity 28 formed in the moveable handle 24.

Figure 6:
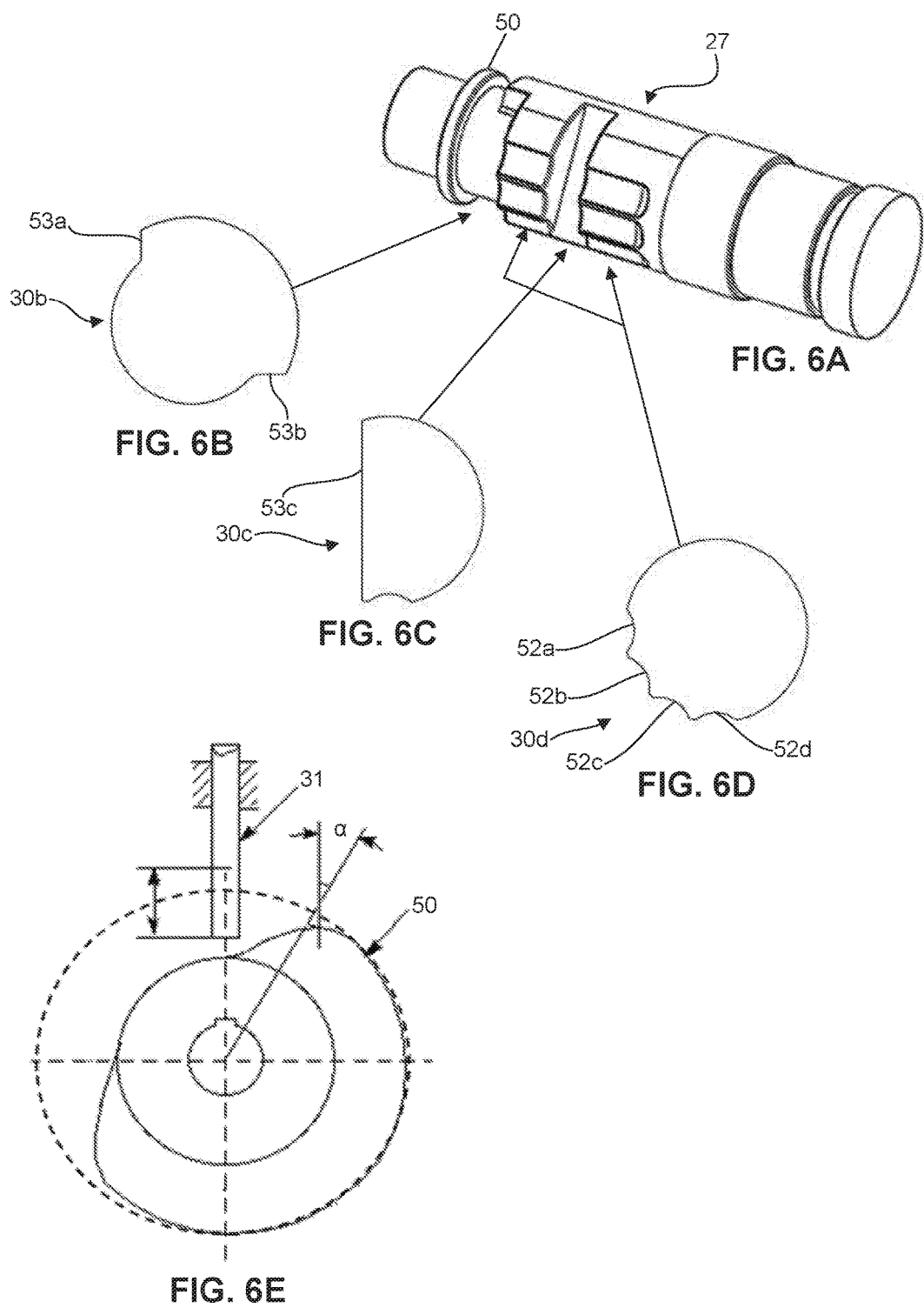
FIG. 6A is a perspective view of a trunnion shaft used in the adjustable connecting device of FIG. 5.
FIG. 6B is an exemplary cross-sectional view of the trunnion shaft at a point.
FIG. 6C is another exemplary cross-sectional view of the trunnion shaft at another point.
FIG. 6D is another exemplary cross-sectional view of the trunnion shaft at another point.
FIG. 6E is a front view at the points corresponding to the cross-sections of the trunnion shaft shown in FIGS. 6B-6D.

As shown in the embodiment of FIG. 6A, around the circumference of the trunnion shaft 27 may be provided with one or more indentations or notches 52a, 52b, 52c, 52d extending In the radial direction. Different rotating cam profiles 30b, 30c, 30d may also be provided by removing material from around the circumference of the trunnion shaft 27. FIGS. 6B-6D show cross-sectional views of the exemplary trunnion shaft 27 at various points along its length. As shown, e.g., in FIG. 6E, one or more detents 31 may be positioned within the cavity to engage the various indentations or notches (52a, 52b, 52c, 52d) and/or cam profiles (30b, 30c, 30d) along the length of the trunnion shaft 27, for example, at the points corresponding to the cross-sections of the trunnion shaft 27 shown in FIGS. 6B-6D. The detents 31 may engage the trunnion shaft 27 so as to limit or resist the rotation of the trunnion shaft 27 and/or prevent movement of the trunnion shaft 27 in certain directions.

Figure 7:
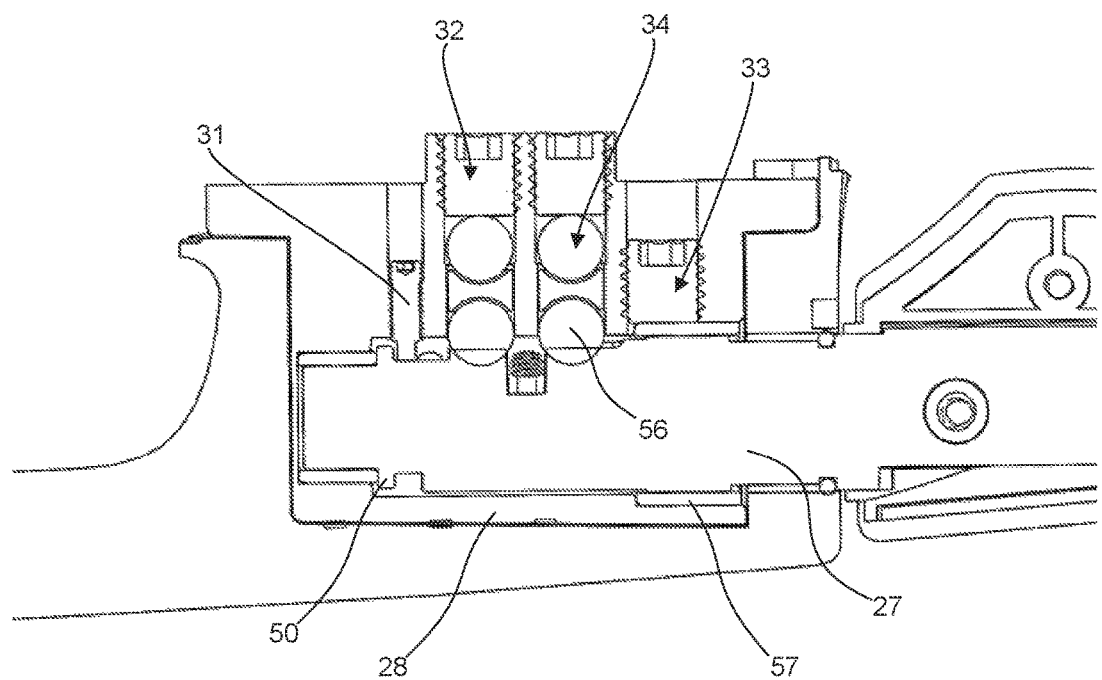
FIG. 7 is a cross-section view of the adjustable connecting device connecting the moveable handle to the stationary handle according to an exemplary disclosed embodiment.
Figure 8:
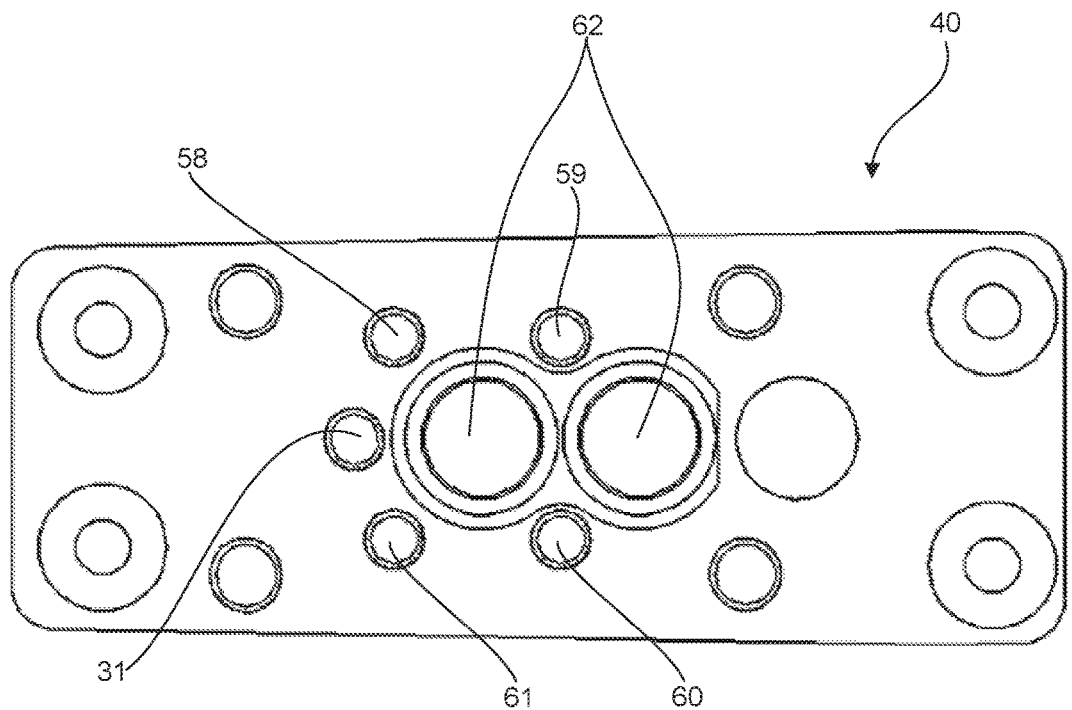
FIG. 8 is a view of the holes in the trunnion housing where detents are inserted to interact with the trunnion shaft used in the adjustable connecting device of FIG. 5, according to an exemplary disclosed embodiment.

In one embodiment, the one or more detents may be set screws. For example, FIG. 7 shows a set screw 31 engaging the trunnion shaft 27 at a position corresponding to the cross-section of FIG. 6B. Set screw 31 may serve at least two purposes. First, the set screw 31 may prevent axial movement of the trunnion shaft 27. For example, set screw 31 may extend inwardly in the radial direction below the outer circumference of the trunnion shaft 27 at all points around the circumference of the trunnion shaft 27, such that a retaining lip 50 formed by the wall of a cam profile may secure the trunnion shaft 27 within the cavity 28 of the stationary handle 21. Second, the rotating cam profiles 30b, 30c, 30d may engage the detent such that the trunnion shaft 27 can only rotate between 0 and 90 degrees with respect to the horizontal. For example, in the cross-section view of the trunnion shaft 27 shown in FIG. 6B, the cam profile 30b may include a horizontal stop face 53a that stops the rotation of the trunnion shaft 27 at 0 degrees with respect to the horizontal when a detent is inserted into its rotational path. If the cam profile includes a horizontal stop face 53a, FIG. 8 shows the mounting hole 58 for such a detent.

The cam profile 30b may also include a vertical stop face 53b that prevents the trunnion shaft 27 from rotating beyond 90 degrees (i.e., past the vertical position) when a detent is inserted in its rotational path. FIG. 8 shows the mounting hole 61 for such a detent. Alternatively, the vertical stop face 53b can be positioned to stop rotation of the trunnion shaft 27 at an angle less than 90 degrees. In the cross-section view of the trunnion shaft 27 shown in FIG. 6C, the cam profile 30c may include a horizontal stop face 53c that stops the rotation of the trunnion shaft 27 at 0 degrees with respect to the horizontal position when a detent is engaged to the top half of horizontal stop face 53c. FIG. 8 shows the mounting hole 59 for such a detent. In addition, a detent may engage the bottom half of horizontal stop face 53c to prevent the trunnion shaft 27 from rotating completely. FIG. 8 shows the mounting hole 60 for such a detent.

In addition to the detent and rotating cam profiles corresponding to FIGS. 6B and 6C, FIG. 7 also shows a set screw 33 that engages the surface of the trunnion shaft 27 or a trunnion bushing 57 surrounding the circumference of the trunnion shaft 27 and providing a lubricious surface for the set screw 33 to rotate against. In this configuration, the set screw 33 presses against the surface of the trunnion shaft 27 or the bushing to generate a variable frictional force that resists rotation of the trunnion shaft 27. During normal use, the friction force can be adjusted so that more or less force is required to rotate the moveable handles 24 between set positions, thereby preventing undesired rotation caused by unintended contact. If desired, the set screw 33 may also be used to fix the trunnion shaft 27 (and attached moveable handle 24) at one specific angle.

In another embodiment, the detent may be implemented by a compression-loaded ball 56 that limits the angular position of the trunnion shaft 27 with respect to the horizontal. For example, FIG. 7 also shows a ball 56 engaging the cross-section of the cam profile 30d shown in FIG. 6D. The ball 56 may be made out of hard plastic or other relatively non-compressible material. Ball 56 may be pressed into one of the four incremental indentations (52a, 52b, 52c, 52d) by a continuous compression force such that the rotation of the moveable handle 24 is limited to, e.g., four incremental angles corresponding to the position of the four incremental depressions on the trunnion shaft 27. In the embodiment of FIG. 7, the continuous compression force is supplied by the set screw 32, pushing against a ball 34 made of rubber or other resilient material, which then transfers the force to the ball 56 in contact with the trunnion shaft 27. The embodiment of FIG. 7 may include two sets of balls mounted in series as shown by holes 62 in FIG. 8. One skilled in the art, however, would readily recognize that the compression force can be supplied in a variety of ways, for example, by a spring-loaded ball bearing.

In another embodiment, a torsion spring (not shown) is attached to the trunnion shaft 27 and arranged in the cavity 28 such that the rotation of the trunnion shaft 27 is limited to some maximum angle with respect to the horizontal. The torsion spring can be made from a material and be of a size such that it prevents the moveable handle 24 from rotating beyond a certain number of degrees. The torsion spring can also be used to automatically return the moveable handle 24 to any home position set by using, for example, one of the detent arrangements described above in connection with FIG. 6. In another embodiment, an elastic cord or elongate spring (not shown) is attached and wrapped around the trunnion shaft 27, then fixed to the far end of the moveable handle 24. The elastic cord can also be used to prevent the moveable handle 24 from rotating beyond a certain number of degrees, and to automatically return the moveable handle 24 to a pre-set angular position.

In another embodiment, the cart 1 further comprises a handle feedback sensor (not shown) that senses the angular position of the moveable handle 24 relative to the stationary handle 21 and/or strain placed on the moveable handle 24 in one of the forward, rearward, or side-to-side directions. Based on the sensor input, a handle feedback controller (not shown) may provide an input to the computer or other equipment on-board the cart 1, such as a steering assistance system. In one embodiment, for example, when the cart 1 is being moved with the moveable handles 24 positioned at 90 degrees (vertical), the handle feedback sensor may unlock a parking brake and/or disable use of the computer as a safety feature. In another embodiment, the handle feedback controller may unlock the computer and/or activate a parking brake when the moveable handles 24 are rotated back to 0 degrees (horizontal).

Because numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

What is claimed is:

1. A cart having an adjustable handle system, the cart comprising:
   a chassis supported on wheels;
   a horizontal work surface having a perimeter defined by at least a front edge, a rear edge, and two side edges;
   a stationary handle connected to, and extending along the perimeter of the horizontal work surface from an origination point located on the rear edge to a connecting point located on one of the two side edges;
   a moveable handle axially coupled to the stationary handle at the connecting point and extending along the perimeter of the horizontal work surface from the connecting point to an end point located on the front edge; and
   an adjustable connecting device connecting the moveable handle to the stationary handle at the connecting point and controlling the angular position of the moveable handle relative to the stationary handle.

2. The cart of claim 1, wherein the adjustable connecting device comprises:
  a trunnion shaft attached to, and extending from the moveable handle into a cavity formed in the stationary handle, the trunnion shaft having indentations in the radial direction; and
  a detent arranged within the cavity to engage the indentations.

3. The cart of claim 2, wherein the detent is a set screw limiting the rotation of the trunnion shaft from 0 to 90 degrees with respect to the horizontal work surface.

4. The cart of claim 2, wherein the detent is compression-loaded ball that limits the angular position of the trunnion shaft with respect to the horizontal work surface to angular increments corresponding to number and position of incremental depressions on the trunnion shaft.

5. The cart of claim 1, wherein the adjustable connecting device comprises:
  a shaft attached to, and extending from the moveable handle into a cavity formed in the stationary handle; and
  a torsion spring attached to the shaft and arranged in the cavity such that the rotation of the trunnion shaft is limited to a maximum angle with respect to the horizontal work surface.

6. The cart of claim 1, wherein the stationary handle is connected to the perimeter of the horizontal work surface only at the origination point and the connecting point, such that the stationary handle and the perimeter of the horizontal work surface are separated by a gap extending the length of the stationary handle between the origination point and the connecting point.

7. The cart of claim 1, further comprising:
  a computer and a display screen;
  a handle feedback controller that monitors the angular position of the moveable handle relative to the stationary handle, wherein
    the handle feedback controller activates a function of the computer, display screen, or touchscreen corresponding to the a pre-programmed angular position of the moveable handle.

* * * * *